(12) United States Patent
Naber et al.

(10) Patent No.: US 8,328,756 B2
(45) Date of Patent: Dec. 11, 2012

(54) ABDOMINAL CAVITY BALLOON FOR PREVENTING A PATIENT'S BLEEDING

(75) Inventors: Eleonora Elisabeth Hendrika Naber, Den Haag (NL); Herman Jozef Theodorus Rutten, Eindhoven (NL); Jazek Jerzy Jakimowicz, Heeze (NL); Richard Hendrik Marc Goossens, Vlaardingen (NL); Cornelis Christiaan Marie Moes, Zeist (NL); Sonja Nandine Buzink, Delfgauw (NL)

(73) Assignee: Technische Universiteit Delft, Delft (NL)

( * ) Notice: Subject to any disclaimer, the term of this patent is extended or adjusted under 35 U.S.C. 154(b) by 357 days.

(21) Appl. No.: 12/126,789

(22) Filed: May 23, 2008

(65) Prior Publication Data

US 2008/0287868 A1 Nov. 20, 2008

Related U.S. Application Data

(63) Continuation-in-part of application No. PCT/NL2006/050297, filed on Nov. 23, 2006.

(30) Foreign Application Priority Data

Nov. 23, 2005 (NL) ..................................... 1030500

(51) Int. Cl.
*A61M 25/10* (2006.01)

(52) U.S. Cl. ............. 604/103.02; 604/94.01; 604/96.01; 604/912; 606/192

(58) Field of Classification Search ............... 604/94.01, 604/95.03, 96.01, 97.01, 912, 915–916, 919, 604/101.01, 101.02; 606/191–192, 195–196, 606/198
See application file for complete search history.

(56) References Cited

U.S. PATENT DOCUMENTS

| | | | | |
|---|---|---|---|---|
| 3,516,407 A | * | 6/1970 | Ruggero | 606/196 |
| 3,570,494 A | * | 3/1971 | Gottschalk | 606/196 |
| 4,338,941 A | * | 7/1982 | Payton | 606/196 |
| 6,024,753 A | | 2/2000 | Claren et al. | |
| 6,607,546 B1 | | 8/2003 | Murken | |
| 2002/0055709 A1 | * | 5/2002 | Weinberger | 604/96.01 |
| 2003/0028097 A1 | | 2/2003 | D'Amico et al. | |
| 2003/0236546 A1 | * | 12/2003 | Packer | 606/193 |
| 2004/0199196 A1 | | 10/2004 | Ravo | |

FOREIGN PATENT DOCUMENTS

| | | |
|---|---|---|
| WO | WO-9915082 | 4/1999 |
| WO | WO-2004069057 | 8/2004 |

* cited by examiner

*Primary Examiner* — Quynh-Nhu H Vu
(74) *Attorney, Agent, or Firm* — Jeffrey D. Myers; Samantha A. Updegraff; Peacock Myers P.C.

(57) ABSTRACT

An abdominal cavity balloon for preventing a haemorrhage in a patient's pelvic region, comprising an inflatable balloon, wherein the balloon is provided with a smooth surface and with a strip that is flexurally stiff and formed to follow the balloon's shape for positioning the balloon.

6 Claims, 2 Drawing Sheets

ABDOMINAL CAVITY BALLOON FOR PREVENTING A PATIENT'S BLEEDING

CROSS-REFERENCE TO RELATED APPLICATIONS

This application is a continuation-in-part application of Patent Cooperation Treaty (PCT) Application Serial No. PCT/NL2006/050297, entitled "Abdominal Cavity Balloon for Preventing a Patient's Bleeding", to Technische Universiteit Delft, filed on Nov. 23, 2006, which itself claims priority to and the benefit of the filing of Netherlands Patent Application Serial No. 1030500, entitled "Abdominal Cavity Balloon for Preventing a Patient's Bleeding", filed on Nov. 23, 2005, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The invention relates to an abdominal cavity balloon for preventing a haemorrhage in a patient's pelvic region, comprising an inflatable balloon.

A possible haemorrhage during abdominal surgery is currently stopped by filling the pelvic cavity with a sufficient amount of sterilised gauze to press the relevant blood vessels shut. This gauze must be removed within 48 hours in order to minimise the risk of infections. The removal of the gauze necessitates a further operation, which puts a considerable strain on the patient and requires all the guarantees inherent to the performance of an operation to be met.

The general aim is to reduce the strain on the patient and to limit the scale of the operation necessary to remove the material needed to inhibit bleeding.

2. Description of Related Art

The U.S. patent publication 2003/0236546 relates to a balloon product for stopping a haemorrhage in the abdominal cavity, in particular a haemorrhage occurring during childbirth. The balloon is provided with an inlet tube for inflating the balloon with air or a physiologic fluid. The balloon is made of a material that is able to expand such as urethane, rubber, silicones, synthetic rubber or vinyl and, when inflated, preferably takes on the shape of a heart so as to allow it to evenly adapt to the space wherein a haemostatic pressure needs to be applied. The surface of the balloon may be coated or impregnated or otherwise provided with a haemostatic coating to control bleeding. The balloon is further provided with a drain tube for removing fluid (blood) from the abdominal cavity. With respect to this drain tube, the U.S. patent publication US 2003/0236546 notes that it should be sufficiently rigid to maintain its inner diameter when the balloon is inflated.

The U.S. patent publication US 2003/0236546 gives no further indication of how to optimise positioning the balloon in the abdominal cavity, nor of how to prevent the balloon from adhering to the tissue in the abdominal cavity.

The device known from the U.S. patent publication 2003/0236546 is, moreover, not designed for use during a surgical operation wherein the abdominal cavity is exposed.

BRIEF SUMMARY OF THE INVENTION

It is the object of the invention to provide such an abdominal cavity balloon to be used during a surgical operation wherein the abdominal cavity is exposed and wherein positioning of the balloon can be realised effectively while, compared to the prior art situation, the strain on the patient is reduced.

To this end the abdominal cavity balloon according to the invention is characterised, in that the balloon is provided with a smooth surface and with a strip that is flexurally stiff and formed to follow the balloon's shape for positioning the balloon.

DETAILED DESCRIPTION OF THE INVENTION

By using the balloon, a pressure that corresponds to the haemorrhage can be applied to the blood vessels, while positioning of the balloon is optimised with the aid of the strip following the balloon's shape. To this end it is essential that the same have sufficient flexural stiffness to allow the balloon to be manipulated into position. When bleeding has stopped and the balloon is no longer needed for combating the haemorrhage, the strip following the balloon's shape also serves for the simple removal in a minimally invasive operation of the balloon from the abdominal cavity. The smooth surface of the balloon facilitates easy removal because it prevents adhesion to the tissue. In this way the strain on the patient is effectively limited.

In a further aspect of the invention, the abdominal cavity balloon is characterised in that the balloon is partitioned into pre-shaped compartments.

In this way a balloon can be provided having an optimised shape and being fully adapted to be used in the abdominal cavity of a patient.

A very suitable embodiment of the abdominal cavity balloon according to the invention is characterised in that there are three sub-compartments, and in that the strip is formed to follow the shape of a first of these compartments, extends in a curve from a second to a third compartment and, during use, projects from there to outside the patient.

In still another aspect of the invention, the abdominal cavity balloon is characterised in that the strip comprises channels for the inlet and outlet of an inflating medium for the balloon.

This is a convenient manner for feeding the balloon, while the amount of pressure supplied can be adjusted precisely to the haemorrhage to be stopped.

The haemostatic properties of the abdominal cavity balloon according to the invention are further enhanced by the measure that the channels are designed for inflating the compartments of the balloon individually.

In still another aspect of the invention, the abdominal cavity balloon is characterised in that the exterior of the balloon is provided with a coagulation-promoting coating.

This further improves the haemostatic properties of the device according to the invention.

BRIEF DESCRIPTION OF THE SEVERAL VIEWS OF THE DRAWINGS

Hereinafter the invention will be further elucidated by way of an exemplary embodiment that does not limit the appended claims, and with reference to the drawing.

The drawing shows in.

Identical reference numerals in the figures refer to similar parts.

Figure 1:
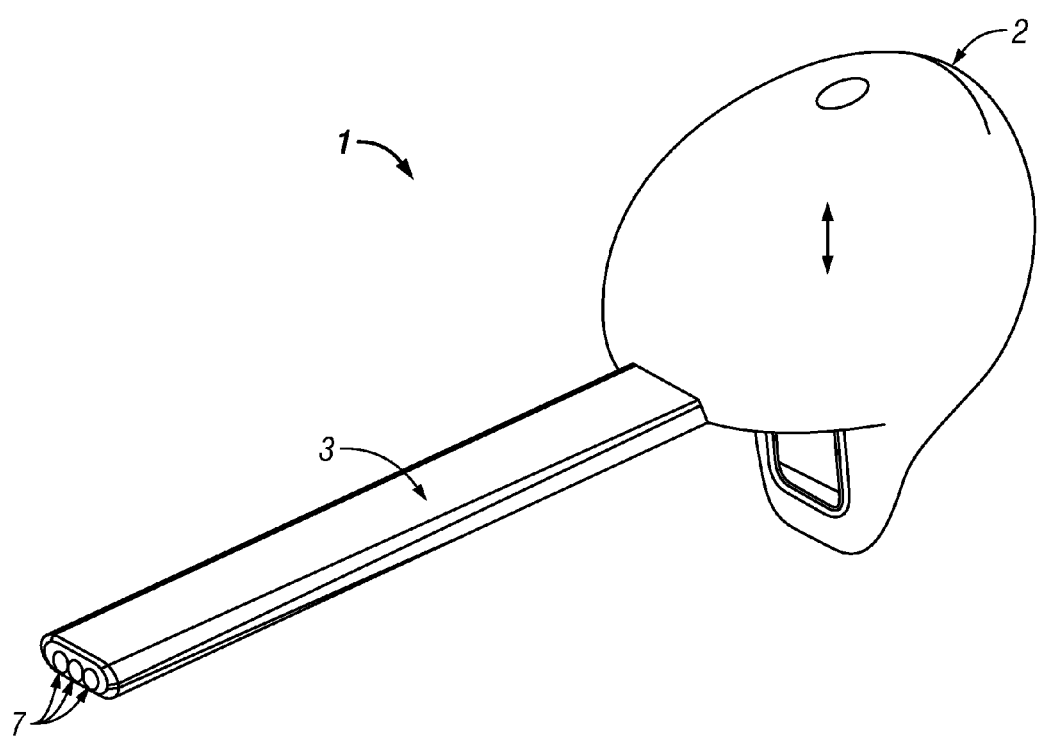
FIG. 1 an elevation of the abdominal cavity balloon according to the invention, and FIG. 2 the abdominal cavity balloon according to FIG. 1 in a perspective transparent view.

Referring first to FIG. 1, reference numeral 1 indicates the abdominal cavity balloon for preventing a haemorrhage in a patient, in accordance with the invention. This abdominal cavity balloon is designed to be used in the pelvic region of the patient and comprises an inflatable balloon 2.

The balloon 2 is provided with a smooth surface and, for positioning the balloon 2, possesses a flexurally rigid strip 3 that follows the balloon's 2 shape.

Figure 2:
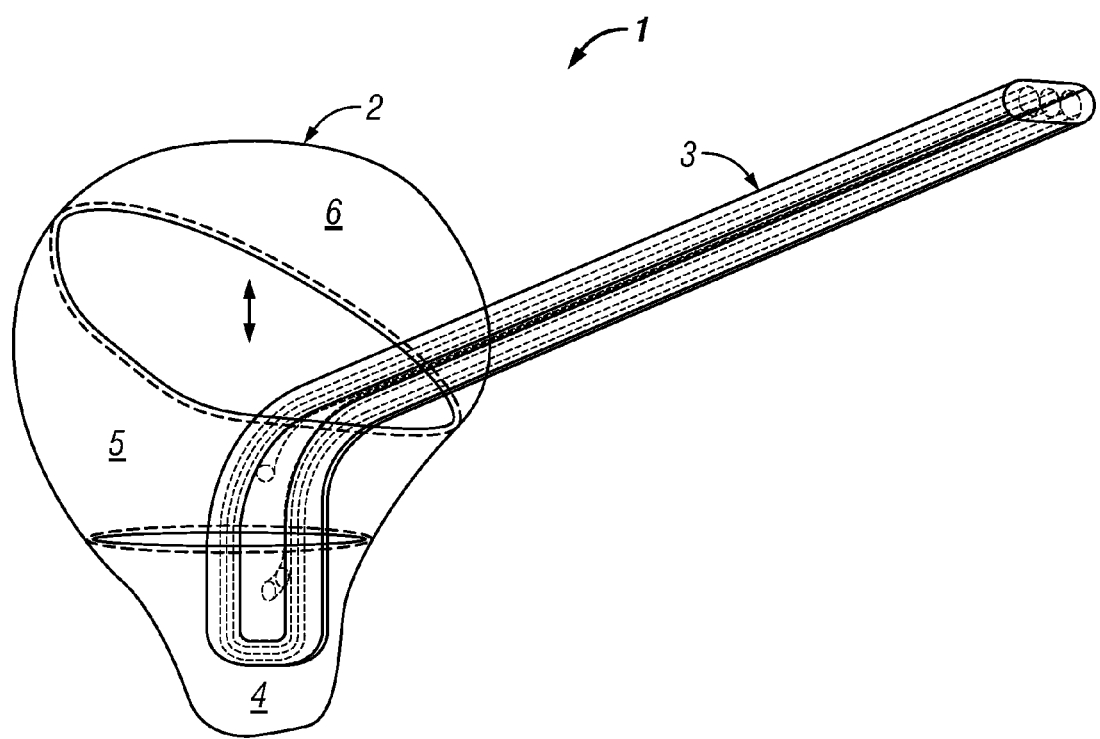

FIG. 2 shows that the balloon 2 is partitioned and embodied with three pre-formed sub-compartments 4, 5 and 6.

To this end the strip 3 is shaped conform a first 4 of these compartments 4, 5, and 6 and extends in a curve from a second 5 to a third compartment 6 wherein, when in use, the strip 3 projects to outside the patient.

The broken lines in FIG. 2 show that in the strip 3 channels are provided for the inlet and outlet of an inflating medium for the compartments 4, 5, and 6 of the balloon 2. In FIG. 1, the openings for these inlet and outlet channels are indicated with reference numeral 7.

The channels are designed for individually inflating the separate compartments 4, 5, and 6 of the balloon 2.

Finally, it should be noted that the exterior of the balloon 2 may be provided with a coagulation-promoting coating.

What is claimed is:

1. An abdominal cavity balloon for preventing a haemorrhage in a patient's pelvic region, comprising:
    an inflatable balloon, said balloon comprising a smooth surface and a strip that is flexurally stiff;
    wherein a first end of said strip engages a surface within said balloon for positioning of said balloon and said first end of said strip does not penetrate through said balloon;
    wherein a second end of said strip extends in a curve conforming to said balloon and then extends away from said balloon surface; and
    wherein during use in the patient's pelvic region said second end of said strip extends from said balloon to an outside of the patient.

2. An abdominal cavity balloon according to claim 1 wherein said strip comprises channels for the inlet and outlet of an inflating medium for said balloon.

3. An abdominal cavity balloon according to claim 2 wherein said channels for are configured so as to provide the inflating medium individual access to said compartments of said balloon individually.

4. An abdominal cavity balloon according to claim 1 wherein an exterior of said balloon is provided with a coagulation-promoting coating.

5. An abdominal cavity balloon according to claim 1 wherein said balloon comprises partitions for partitioning said balloon into pre-shaped compartments.

6. An abdominal cavity balloon according to claim 5 wherein said balloon comprises first, second, and third compartments and wherein said strip engages a surface of said first, second, and third compartments.

* * * * *